(12) United States Patent
Mitelberg et al.

(10) Patent No.: US 7,708,704 B2
(45) Date of Patent: May 4, 2010

(54) INTERVENTIONAL MEDICAL DEVICE COMPONENT HAVING AN INTERRUPTED SPIRAL SECTION AND METHOD OF MAKING THE SAME

(75) Inventors: Vladimir Mitelberg, Austin, TX (US); John H. Thinnes, Jr., Miami, FL (US); Keith Balgobin, Pembroke Pines, FL (US); William W. Sowers, Pembroke Pines, FL (US)

(73) Assignee: Codman & Shurtleff, PC, Raynham, MA (US)

( * ) Notice: Subject to any disclaimer, the term of this patent is extended or adjusted under 35 U.S.C. 154(b) by 756 days.

(21) Appl. No.: 11/461,219

(22) Filed: Jul. 31, 2006

(65) Prior Publication Data

US 2008/0097398 A1    Apr. 24, 2008

(51) Int. Cl.
*A61B 5/00* (2006.01)
*A61F 2/24* (2006.01)
*A61M 5/178* (2006.01)
*A61M 25/00* (2006.01)

(52) U.S. Cl. .............. 600/585; 623/1.11; 604/164.13; 604/264; 604/528

(58) Field of Classification Search ............. 600/585; 623/1.11; 604/164.13, 264, 528
See application file for complete search history.

(56) References Cited

U.S. PATENT DOCUMENTS

| | | | |
|---|---|---|---|
| 3,547,103 A | 12/1970 | Cook | |
| 4,830,002 A | 5/1989 | Semm | |
| 5,108,407 A | 4/1992 | Geremia et al. | |
| 5,250,071 A | 10/1993 | Palermo | |
| 5,397,304 A | 3/1995 | Truckai | |
| 5,624,449 A | 4/1997 | Pham et al. | |
| 5,725,549 A | 3/1998 | Lam | |
| 5,749,894 A | 5/1998 | Engelson | |
| 5,910,144 A | 6/1999 | Hayashi | |
| 5,989,242 A | 11/1999 | Saadat et al. | |
| 6,027,863 A * | 2/2000 | Donadio, III | 430/320 |
| 6,107,004 A | 8/2000 | Donadio, III | |
| 6,123,720 A * | 9/2000 | Anderson et al. | 623/1.12 |
| 6,280,464 B1 | 8/2001 | Hayashi | |
| 6,338,736 B1 | 1/2002 | Boosfeld et al. | |
| 6,428,489 B1 * | 8/2002 | Jacobsen et al. | 600/585 |
| 6,478,773 B1 | 11/2002 | Gahndi et al. | |
| 6,585,718 B2 | 7/2003 | Hayzelden et al. | |
| 6,749,560 B1 * | 6/2004 | Konstorum et al. | 600/143 |
| 6,761,733 B2 | 7/2004 | Chobotov et al. | |
| 6,953,472 B2 | 10/2005 | Palmer et al. | |
| 7,033,374 B2 | 4/2006 | Schaefer et al. | |
| 7,044,134 B2 | 5/2006 | Khairkhahan et al. | |
| 2003/0125709 A1 | 7/2003 | Eidenschink | |

(Continued)

*Primary Examiner*—Max Hindenburg
*Assistant Examiner*—John Pani
(74) *Attorney, Agent, or Firm*—Cook Alex Ltd.

(57) ABSTRACT

A component for use as or for incorporation within a medical instrument navigable through body vessels of a human subject is provided. The component includes a tubular portion with an interrupted spiral defined by alternating cut and uncut sections. The sum of the arcuate extents of each bridge section and a cut section adjacent to the bridge section in end-to-end fashion is neither a whole number factor of 360 degrees nor a multiple of 90 degrees; this provides uniform rigidity, flexibility, and stretch resistance in all bending planes. The device further includes multiple sections, the pitch of the spiral varying from section to section in order to vary the sections' flexibilities.

17 Claims, 4 Drawing Sheets

U.S. PATENT DOCUMENTS

| | | |
|---|---|---|
| 2004/0006363 A1 | 1/2004 | Schaefer |
| 2004/0111095 A1 | 6/2004 | Gordon et al. |
| 2005/0171572 A1 | 8/2005 | Martinez |
| 2005/0177132 A1 | 8/2005 | Lentz et al. |
| 2005/0216018 A1 | 9/2005 | Sennett |
| 2006/0004346 A1 | 1/2006 | Begg |
| 2006/0100687 A1* | 5/2006 | Fahey et al. ................. 623/1.11 |
| 2006/0116714 A1 | 6/2006 | Sepetka et al. |
| 2006/0121218 A1 | 6/2006 | Obara et al. |

* cited by examiner

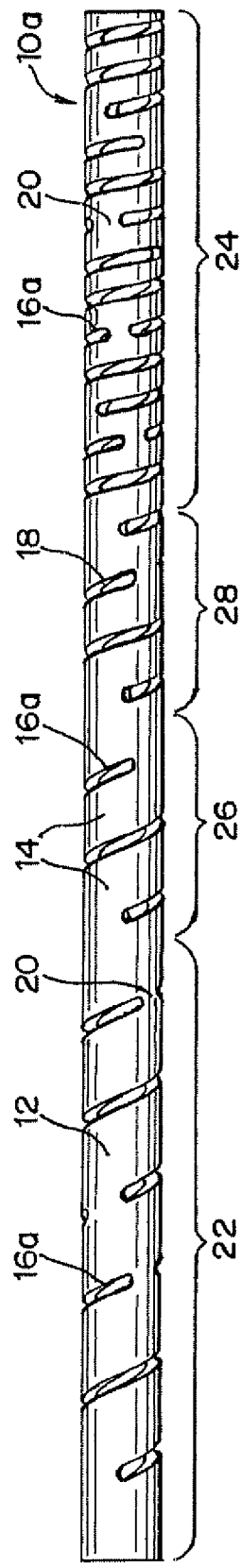
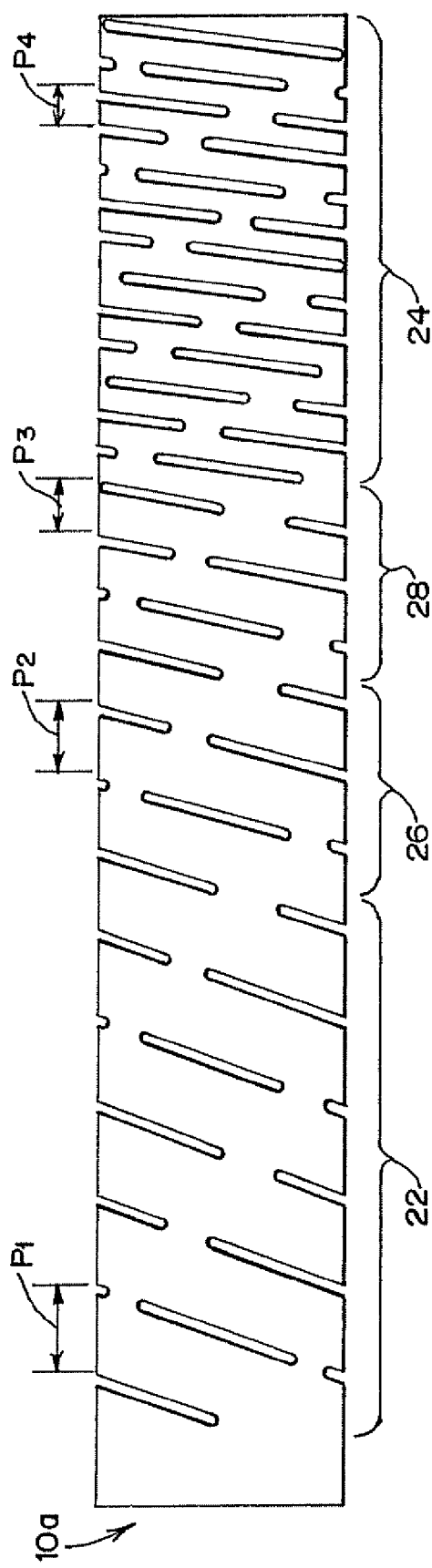

INTERVENTIONAL MEDICAL DEVICE COMPONENT HAVING AN INTERRUPTED SPIRAL SECTION AND METHOD OF MAKING THE SAME

FIELD OF THE INVENTION

This invention generally relates to medical devices that are navigable through body vessels of a human subject. More particularly, this invention relates to tubular devices having an interrupted spiral section and methods of making the same.

DESCRIPTION OF RELATED ART

A number of medical procedures require the introduction of tubing to a body vessel. For example, vessel defects, such as blockages and stenoses, within the human vasculature system are often treated by the intraluminal delivery of treatment fluids or implants, such as expandable stents and embolic coils. Implants can take any of a number of forms and may be delivered to a diseased site in a number of manners. According to one known method of delivering a medical implant, the distal end of a flexible catheter is positioned adjacent to a target site of a body vessel, such as an aneurysm. Once the catheter is properly positioned, a delivery/detachment system is passed through a lumen of the catheter until a distal end of the delivery system exits the distal end of the catheter in the area of the target site. An implant, such as an embolic coil, carried at the distal end of the delivery/detachment system is thereafter released to the diseased site.

The path to the target site is typically tortuous, so the catheter is preferably relatively flexible to allow it to pass through the vasculature to the desired site. Conversely, the catheter may be required to pass through constricted vessels, so it is also desirable for it to be at least somewhat rigid. When the catheter has been properly positioned, the delivery system must follow the path defined by the catheter, so the delivery system also preferably has similar characteristics of flexibility and rigidity.

Tubing having at least a portion defined by a wound spring or a spiral-cut tube can provide desired levels of flexibility and rigidity, but for some applications it may be desirable for the tubing to offer some anti-elongation or stretch resistance characteristics. For these types of applications, wound spring or spiral-cut portions are unsuitable because they have the tendency to elongate or stretch. Attempts to modify continuously cut spiral approaches include U.S. Patent Application Publication No. 2006/0100687 to Fahey et al. This proposes self-expanding stent delivery using inner and outer elongated shells having slots interrupted by solid struts which can be oriented in uniformly spaced helical patterns.

A general aspect or object of the present invention is to provide a medical device component with flexibility, rigidity, and anti-elongation or stretch resistance characteristics.

Another aspect or object of this invention is to provide a medical device component with generally uniform flexibility in any bending plane and which are sized and configured for neurovascular delivery systems.

Another aspect or object is to provide medical device components that exhibit generally uniform bendability, flexibility, rigidity, and anti-elongation or stretch resistance characteristics in all bending planes.

Another aspect or object of this invention is to provide a method of manufacturing a medical device component with selectable flexibility, rigidity, and anti-elongation or stretch resistance characteristics.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with one embodiment or aspect of the present invention, a component of an interventional medical device operable while within a body vessel is provided with a generally hollow tubular portion. The tubular portion includes a spiral ribbon having adjacent turns. The ribbon is defined by a helically oriented pathway of a plurality of open sections alternating with a plurality of bridge members in end-to-end fashion. The spiral ribbon defines a relatively rigid region, a relatively flexible region, and a transition region between the relatively rigid region and the relatively flexible region.

According to another embodiment or aspect of the present invention, a neurovascular implant delivery system device movable through a microcatheter within a body vessel is provided with a generally hollow tubular portion. The tubular portion includes a spiral ribbon having adjacent turns. The ribbon is defined by a helically oriented pathway of a plurality of open sections alternating with a plurality of bridge members in end-to-end fashion. Each bridge member is out of axial alignment with an adjacent bridge member of the helically oriented pathway.

According to yet another aspect of the present invention, a method of creating a component of an interventional medical device operable while within a body vessel is provided that includes providing a tubular member and a cutting member. The cutting member is alternated between a cutting mode, in which it cuts the tubular member to create a cut section, and a non-cutting mode, in which it is prevented from cutting the tubular member to create an uncut section. At least one of the cutting member and the tubular member is moved through a first angle defining a substantially helical path with respect to the other while the cutting member is alternated between modes. The simultaneous movement and switching between modes results in an interrupted spiral with sections alternating between cut and uncut sections in a first region. In embodiments exhibiting a plurality of varying helical pathways, the first angle is then changed to a second angle, while continuing to alternate between modes to create an interrupted spiral in a second region. The second angle is then changed to a third angle, while continuing to alternate between modes to create an interrupted spiral in a third region.

Special application for the present invention has been found for tubular portions of medical device guidewires, catheters, microcathers, fine-bore guiding cathers, and embolic coil/implant delivery, detachment or retrieval systems. One such application is illustrated in an application entitled "Interventional Medical Device System Having an Elongation Retarding Portion and Method of Using the Same" (Ser. No. 11/461,231), filed herewith on Jul. 31, 2006, which is hereby incorporated herein by reference. However, the present invention is also applicable to tubular components of other devices adapted for movement through body lumens, so it will be understood that certain embodiments of the products and methods described herein are not limited to particular medical devices or particular surgical applications.

BRIEF DESCRIPTION OF THE DRAWINGS

FIG. 5 is a front elevational view of a medical device portion according to another aspect of the present invention;

FIG. 6 is a front elevational view of the medical device portion of FIG. 5, in an unrolled condition.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
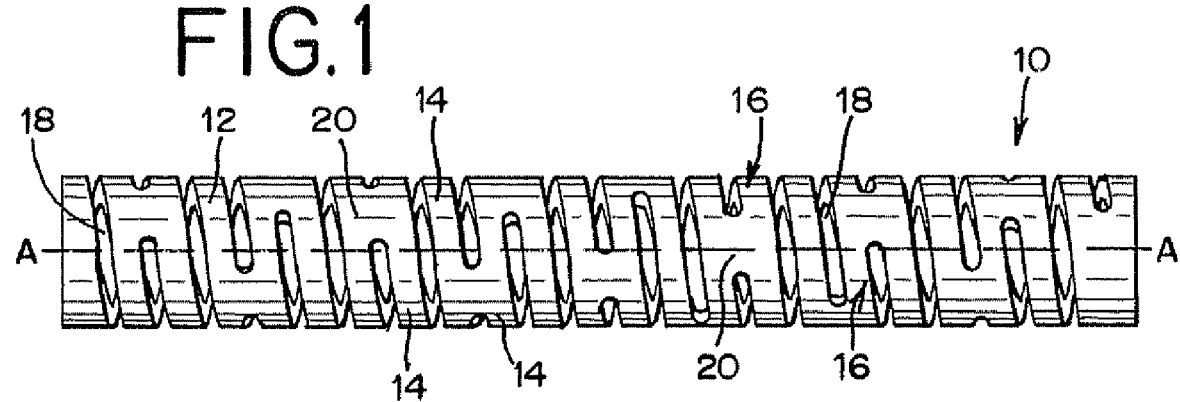
FIG. 1 is a front elevational view of a medical device portion according to an aspect of the present invention.
Figure 2:
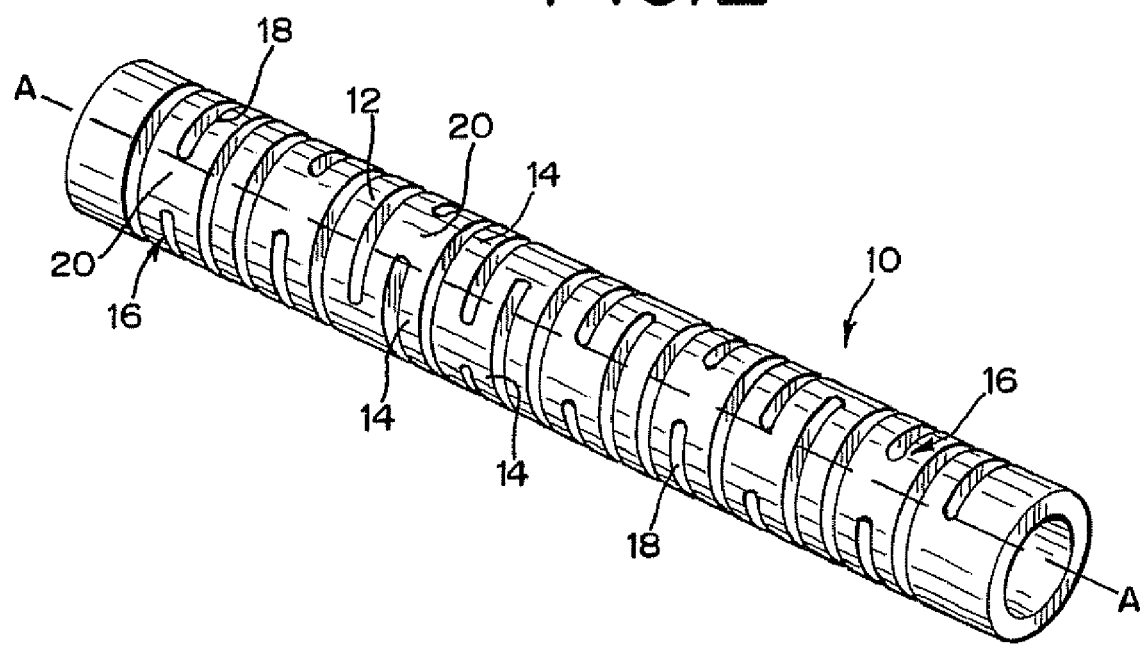
FIGS. 2 and 3 are front perspective views of the medical device portion of FIG. 1.
Figure 3:
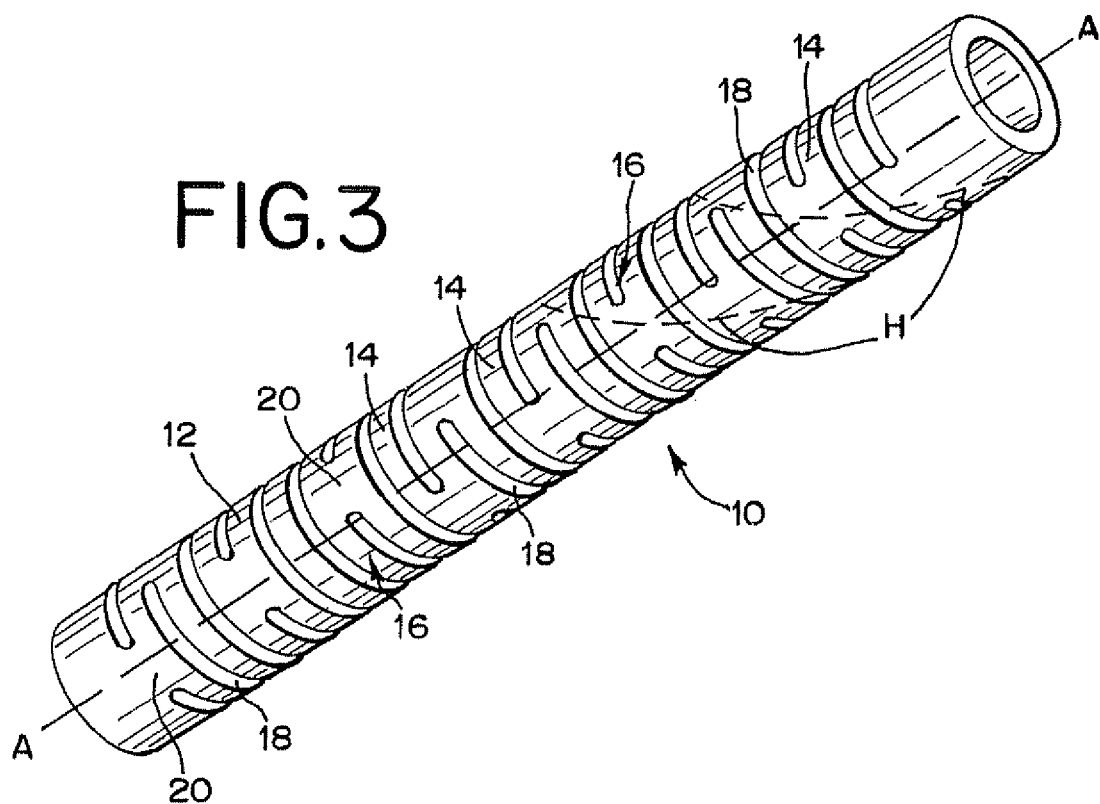

FIGS. 1-3 illustrate a generally hollow or tubular structure according to the present invention. When used herein, the terms "tubular" and "tube" are to be construed broadly and are not limited to a structure that is a right cylinder or strictly circumferential in cross-section or of a uniform cross-section throughout its length. For example, the tubular component or device is generally designated at 10 and shown as a substantially right cylindrical structure. However, the tubular component 10 may have a tapered or curved outer surface without departing from the scope of the present invention.

The component 10 is adapted to be received by a body vessel as a component or part of a medical device guidewire, detachment system, deployment system, catheter or other medical instrument or device as generally discussed herein. The illustrated component 10 includes a generally hollow tubular portion or member with a spiral ribbon 12 having adjacent turns 14. A typical wound ribbon is formed from a hypotube to provide a spiral-cut tube that has a plurality of coils or turns that are defined by a helical cut, opening, or separation. However, the turns 14 of the component 10 are substantially defined and separated by an interrupted spiral 16, which is characterized by alternating open or cut sections 18 and uncut sections or bridge members 20.

Figure 4:
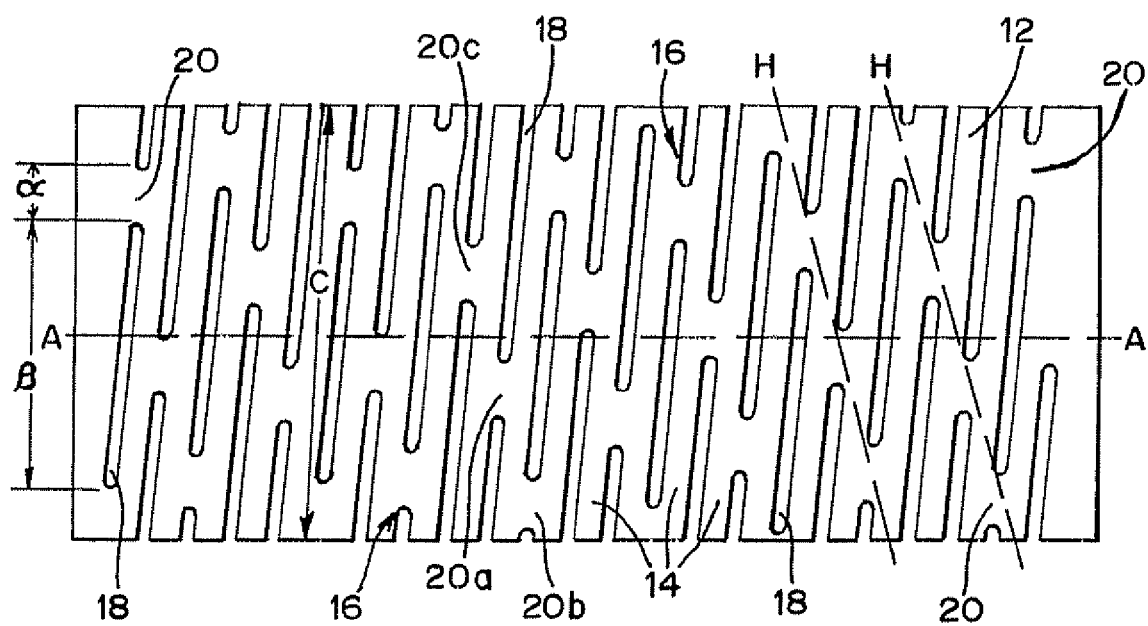
FIG. 4 is a front elevational view of the medical device portion of FIGS. 1-3, in an unrolled condition.

The pathway of the alternating cut and uncut sections 18 and 20 is angled with respect to a right circumference "C" of the component 10 (illustrated in laid-out fashion in FIG. 4). This pathway preferably follows a single substantially helical pattern, which simplifies manufacture of the component 10, as described below. The presence of the bridge member-containing pathway makes the component 10 more stretch resistant than a typical wound ribbon or spiral cut tube.

In the embodiment of FIGS. 1-3, each helically oriented uncut section or bridge member 20 has an arcuate extent "α" (illustrated in laid-out fashion in FIG. 4), and each helically oriented cut section 18 has an arcuate extent "β" (illustrated in laid-out fashion in FIG. 4). When used herein, the term "arcuate extent" refers to the angle between longitudinal projections of the endpoints of a helical element (e.g., a bridge member 20 or a cut section 18) about or with respect to a longitudinal axis "A" of the component 10. Such projection-defined arcuate extents provide accurate relative lengths for the respective elements as they actually exist along the continuous helical path. In the same way, the circumference "C" of the component 10 has an arcuate extent of 360° about the longitudinal axis "A", with circumference "C" not being helically oriented, with the projection of a full turn along the helical path being a 360° circumference.

Preferably, the bridge members are distributed so as to avoid positioning adjacent bridge members 20 of the tube in axial alignment with each other in one or more rows along a direction parallel to the longitudinal axis "A". Such an arrangement is not preferred because it causes the device to have a bending preference, with each row of thus aligned bridge members acting as a hinge. A device with a bending preference is especially rigid in one plane, due to the presence of aligned bridge members that are aligned along a line parallel to the axis of the device, and especially flexible in another plane, due to the absence of any bridge members. Accordingly, such a device may be awkward to use, because it must be rotated to properly orient the flexible plane to navigate a curve of a body vessel.

Examples of devices having bending preferences are shown in U.S. Patent Application Publication No. 2005/0216018 to Sennett. Also, U.S. Patent Application Publication No. 2005/0177132 to Lentz shows a plurality of slits that are axially offset with respect to each other, rather than lying along a continuous helical pathway. These references and any others referenced herein are hereby incorporated herein by reference.

In contrast, the illustrated component 10 of FIGS. 1-3 has bridge members 20 that are defined herein as "staggered"; that is, each is out of alignment along a line parallel to the axis of the device with at least one, and preferably both, bridge members 20 immediately adjacent thereto. More particularly, FIG. 4 shows the component 10 in an unrolled or laid-out condition. An exemplary staggered arrangement is shown, with staggered bridge member 20a being out of axial alignment with both staggered adjacent bridge members 20b, 20c. FIG. 4 also shows an embodiment in which the sum of the arcuate extent or projection "α" of a bridge member 20 and of the arcuate extent or projection "β" of one adjacent cut section 18 is between 180° and 360°. However, the sum may also be less than 180° or greater than 360°, depending on the desired performance characteristics, as will be described in greater detail herein.

In one embodiment, the arcuate extent or projection "α" of each helically oriented bridge member 20 is in the range of approximately 10° and approximately 65°, and the arcuate extent or projection "β" of each cut section 18 is in the range of approximately 45° and approximately 270°. It has been found that an arcuate extents "α" and "β" of approximately 45° and 220°, respectively, are suitable for a component incorporated into an embolic coil delivery system passed through a catheter to a target site of the neurovascular system. Other arcuate extents or projections "α" and "β" may be preferred for other applications.

Rather than being aligned along a direction parallel to the longitudinal axis "A", the illustrated bridge members 20 are staggered in a substantially helical pattern "H", as shown in FIGS. 3 and 4. For a component 10 having a set of identical alternating cut sections 18 and uncut sections or bridge members 20 along a single spiral path, as in FIG. 4, the helical pattern "H" is achieved by assuring that the sum of the arcuate extent "α" of a helically oriented bridge member plus the arcuate extent "β" of an adjacent helically oriented cut section 18 is neither a factor of 360° (typically 90° or 180°), nor a multiple of 90°. If the sum of the arcuate extents "α" and "β" of such a helically continuous bridge member 20 and adjacent cut section 18 is a factor of 360° or a multiple of 90°, then the component 10 will have one or more axially aligned rows of bridge members 20, which may include adjacent bridge members. Axially aligned rows of bridge members create a disadvantageous bending preference according to the description herein.

By staggering or separating the bridge members 20 from each other, especially when combined with having the bridges positioned along adjacent helical turns of the device, the component 10 more evenly distributes the bridge members 20 without preference for bending plane, which promotes uniform rigidity, flexibility, and stretch resistance in all bending planes. This may be preferred, because a medical device incorporating the component 10 need not be rotated into a particular orientation to navigate a curved portion of a body vessel. For example, such a device having such a component can follow the twists and turns of a guiding catheter without the need to rotate the device every time a twist or turn is encountered, which could be especially important when navigating the neurovascular system.

The arcuate extents "α" and "β" of the helically oriented bridge members 20 and cut sections 18 may be varied as desired to increase or decrease the rigidity, flexibility, and stretch resistance of the component 10. This is referred to herein as "length modulation" of the interrupted spiral. This is only one manner of adjusting the performance characteristics of the component, which may also be varied by, for example, changing the number of bridge members ("frequency modulation") or the pitch of the interrupted spiral ("pitch modulation"). These methods may be used to give different portions of the component differing performance characteristics.

It may be preferred, for example, to provide a component that is more rigid at a proximal portion, to improve column strength and pushability, and more flexible at a distal portion, to improve trackability and provide a relatively atraumatic distal tip. In one embodiment, illustrated in FIG. 5, a distal portion of a component 10a has a "pitch-modulated" interrupted spiral 16a. FIG. 6 shows the portion in an unrolled or laid-out condition. The interrupted spiral 16a may comprise a distal end of device into which the component 10a is incorporated, defining approximately the distal-most 15-30% (preferably 20%) of the device. This relative length relationship is also preferred for any interrupted spiral according to the present invention, including the embodiments of FIGS. 1-4. In one embodiment, the interrupted spiral comprises the distal-most 40 cm of a 200 cm neurovascular implant delivery system device, with the proximal-most portion comprising an uncut tubular portion. The delivery system device preferably is comprised of a stainless steel hypotube and has an outer diameter no greater than 0.025 inch, preferably no greater than 0.20 inch, and most preferably the outer diameter is approximately 0.0132 inch.

The illustrated "pitch-modulated" interrupted spiral 16a has a varying pitch that decreases distally from a relatively rigid region 22 to a relatively flexible region 24. The pitch $P_4$ of the turns of the interrupted spiral 16a in the flexible region 24 may be, for example, in the range of 20-75% (preferably about 40%) that of the pitch $P_1$ of the turns in the rigid region 22. In one embodiment, which is especially suitable for use in a neurovascular implant delivery system device, the pitch $P_1$ of the turns in the rigid region 22 is in the range of approximately 0.015 inch and approximately 0.025 inch (preferably about 0.02 inch), compared to a pitch $P_4$ of the turns in the flexible region 24 in the range of approximately 0.004 inch and approximately 0.006 inch (preferably about 0.0045 inch).

It may be preferred to provide one or more transition regions between the rigid and flexible regions 22 and 24, to form a region of intermediate rigidity that effectively creates a rigidity gradient. For example, FIGS. 5 and 6 show two transition regions, a proximal transition region 26 and a distal transition region 28 between the rigid and flexible regions 22 and 24. The proximal transition region 26 is more flexible than the adjacent rigid region 22, but less flexible than the distal transition region 28 which, in turn, is less flexible than the adjacent flexible region 24.

In one embodiment of a "pitch-modulated" interrupted spiral, the rigidity may be decreased by providing a pattern whereby the pitch of the successive regions decreases nonlinearly. For example, a "pitch-modulated" interrupted spiral 16a may include a proximal transition region 26 having a pitch $P_2$ having its turn or turns in the range of about 75-90% (preferably about 80%) that of the rigid region 22, a distal transition region 28 having a pitch $P_3$ having its turn or turns in the range of about 70-80% (preferably about 75%) that of the proximal transition region 26, and a flexible region 24 having a pitch $P_4$ having its turn or turns in the range of 60-70% (preferably about 66%) that of the distal transition region 28. More particularly, for an interrupted spiral having a pitch $P_1$ (FIG. 6) in the rigid region 22 of approximately 0.015 inch and a pitch $P_4$ in the flexible region 24 of approximately 0.006 inch, the interrupted spiral 16a may have a pitch $P_2$ of approximately 0.012 inch in the proximal transition region 26 and a pitch $P_3$ of approximately 0.009 inch in the distal transition region 28. Each transition region may be relatively short, comprising between one and four turns, preferably at least two turns, for example.

A component 10a according to the preceding description is particularly applicable to a delivery system device for positioning and the controlled release of neurovascular implants, such as embolic coils and stents, for the treatment of intracranial aneurysms, arteriovenous malformations, and arteriovenous fistulae. In such applications, the component 10a may be incorporated into a delivery system device pushed through a pre-positioned microcatheter with a distal end at a target site within the neurovasculature. The delivery system device has an outer diameter no greater than about 0.025 inch, preferably no greater than about 0.150 inch, and preferably has an outer diameter of approximately 0.0132 inch.

The rigid region 22 allows the delivery system device to be pushed through the microcatheter without collapsing or "snaking," while the flexible region 24 allows the delivery system device to follow the path defined by the microcatheter. A similar effect may be achieved by maintaining a uniform pitch, while decreasing the number ("frequency modulation") or arcuate extent ("length modulation") of the bridge members from left to right, in the orientation of FIGS. 5 and 6. Furthermore, these methods of varying the rigidity of the component may be practiced in combination with each other, such as by decreasing the pitch of the interrupted spiral and the arcuate extent of the bridge members. Additionally, the distal end of the component 10a may be made especially flexible by providing a flexible region 24 at least partially comprised of a continuous spiral that is free of bridge members.

Figure 7:
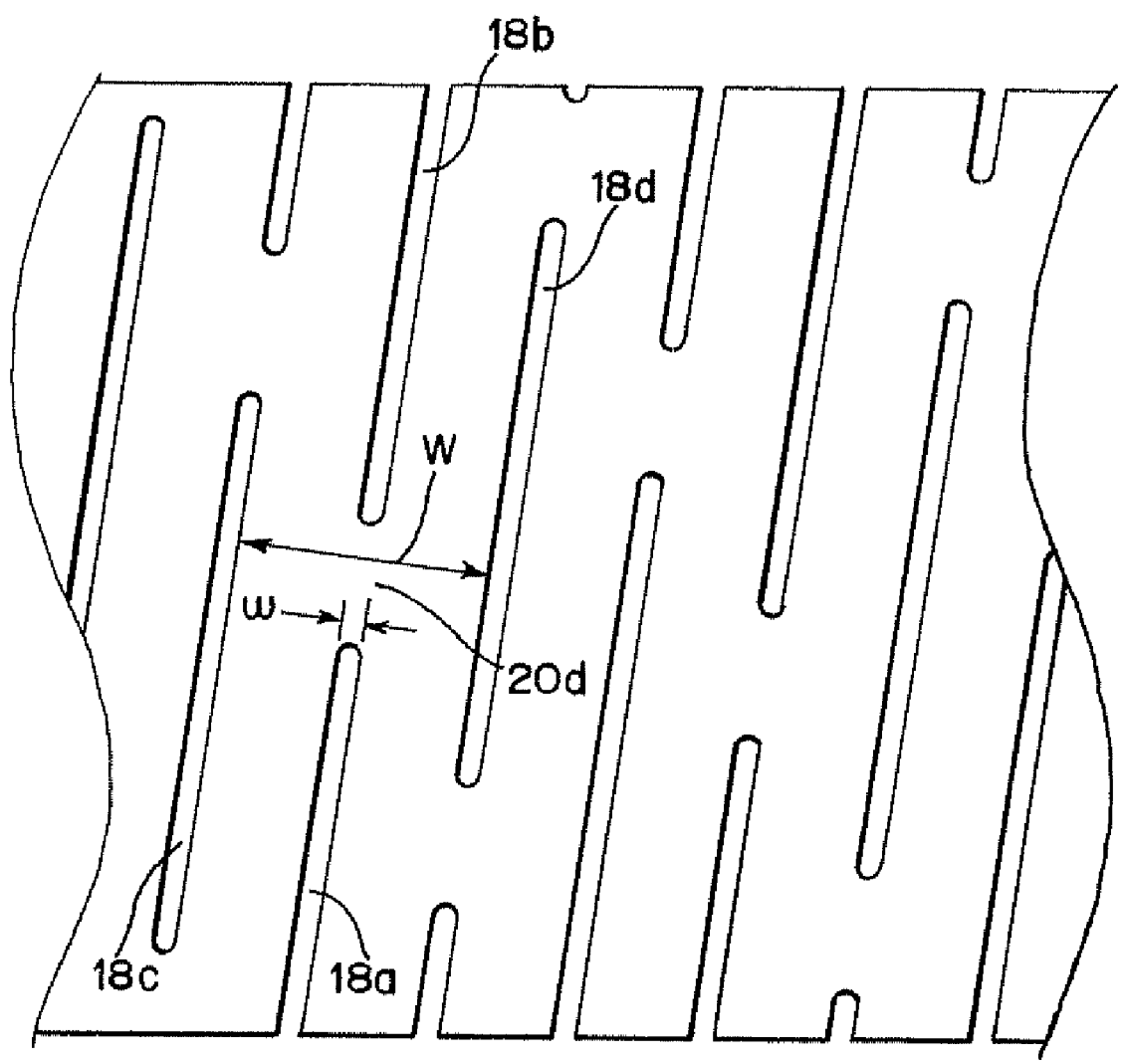
FIG. 7 is a detail view of an interrupted spiral of a medical device component according to an aspect of the present invention.

Preferably, the bridge members of any interrupted spiral according to the present invention are sufficiently strong enough to resist fracturing at pull forces likely to be experienced by the component in the body. The minimum strength varies depending on a number of factors, including the nature of the device into which the component is incorporated and the conditions of the subject body vessel. Hence, the minimum strength to ensure the integrity of the bridge members can vary over a wide range, for example, between approximately 0.1 lbf to more than 1 lbf. If the bridge members are too narrow or weak, then they may fracture during use, thereby allowing the device to elongate, which may be undesirable for certain applications. Also avoided by the present designs is the possibility of debris from fractured bridges entering the body vessel. A typical longitudinal width "ω" of a bridge member 20d (FIG. 7), equivalent to the kerf of the laterally adjacent open sections 18a and 18b that help to define same, is between about 0.0005 inch and about 0.0015 inch, most preferably approximately 0.001 inch for a component incorporated into a neurovascular implant delivery system device. Measured differently, as the separation between longitudinally spaced cut sections 18c and 18d, the bridge member 20d may have a width "W" of approximately 0.0109 inch, in the case of a 0.006 inch pitch pattern for a component having an outer diameter of approximately 0.0132 inch.

As described herein, the component includes a plurality of open sections 18, but a component according to certain aspects of the present disclosure may be useful in medical devices requiring a substantially closed tube. For example, neurovascular balloon microcatheters must have a closed tube in order to allow inflation fluid to be delivered to the associated balloon without leakage. In order to incorporate a component according to the present invention into such a medical device, the interrupted spiral portion 16 may be covered by a substantially non-porous layer, sleeve, or film, externally, internally or even both. Preferably, such a layer is sufficiently non-porous to prevent leakage of an inflation or treatment fluid, and also relatively thin and flexible to prevent excessive altering of the performance characteristics of the interrupted spiral portion 16.

FIG. 4 shows the component 10 in an unrolled or laid-out condition, and it will be appreciated that the component 10 may be formed by creating the interrupted spiral 16 in a flat sheet, then rolling and sealing the sheet into the tubular configuration of FIGS. 1-3. Similarly, the component 10a of FIG. 5 may be formed by rolling and sealing the sheet of FIG. 6 into a tubular configuration. The cut sections 18 may be formed by laser-cutting or other means, depending on the material of the sheet. Alternatively, the interrupted spiral 16, 16a may be formed by providing a wound wire, with adjacent coils being joined by spot welds serving as the bridge members 20. Hence, when used herein, the term "cut section" is not limited to an open arc formed by cutting, but includes any open arc, whether created by cutting a tube, winding a wire, etching, photoresist, or any other method.

According to a preferred method of manufacturing the component, a hollow tubular member and a cutting member are provided. The nature of the cutting member depends on the material of the hollow tubular member, but a laser is a suitable cutting member for use with a metallic tubular member. In the case of a stainless steel tubular member suitable for use in delivering a neurovascular implant, i.e. a tubular member having an outer diameter no greater than 0.025 inch, the laser may be adapted to provide a kerf in the range of about 0.0005-0.0015 inch (preferably 0.001 inch). The cutting member is operated for a selected duration to create a cut section in the tubular member, and then for a duration during which cutting the tubular member is prevented. The cutting member is typically prevented from cutting the tubular member by deactivating it for a selected period of time. The steps of cutting the tubular member and deactivating the cutting member are alternated while at least one of the tubular member and the cutting member is moved in a substantially helical path with respect to the other. This movement will cause the cutting member to create an interrupted spiral in the tubular member, with the bridge members being created during the time when the cutting member is deactivated. Preferably, the cutting member is operated so as to create staggered or separated bridge members according to the description herein.

The helical movement of the above method may be accomplished in a variety of ways, such as by rotating the cutting member about the tubular member or by fixing the cutting member and rotating the tubular member on a mandrel. The helical movement may also be achieved by moving both members, such as by rotating the tubular member while moving the cutting member axially with respect to the rotating tubular member.

Addition steps are required to create a component having a varying rigidity. For example, in order to form the component 10a of FIGS. 6 and 7, the rotational angle through which the cutting member and/or the tubular member is moved must be changed for each region. The angle is relatively steep for the rigid region 22, and is made progressively shallower at each successive region, until it is at its most shallow orientation for the flexible region 24. Of course, the angle is changed from relatively shallow to relatively steep orientation if the interrupted spiral 16a is formed beginning with the flexible region 24 and ending with the rigid region 22. Varying rigidity by other means, e.g. frequency or length modulation, also requires additional steps, typically involving changing the frequency and/or duration of alternating between forming cut and uncut sections.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A component of an interventional neurovascular implant medical device, the component being movable through a micro-catheter within a body neurovascular vessel, comprising:

a generally hollow tubular portion including a spiral ribbon having adjacent turns, said ribbon being between a helically oriented pathway of a plurality of open sections alternating with bridge members in end-to-end fashion along the helically oriented pathway, each bridge member being out of axial alignment with each bridge member immediately adjacent thereto, wherein said spiral ribbon defines a relatively rigid region, a relatively flexible region, and a first transition region between the relatively rigid region and the relatively flexible region, wherein the helically oriented pathway has a first pitch in the relatively rigid region, a second pitch in the relatively flexible region, and a third pitch in the first transition region, the first pitch being greater than the third pitch and the third pitch being greater than the second pitch, and wherein each bridge member has an arcuate extent in a range of approximately 10° and approximately 65°, wherein each cut section has an arcuate extent in a range of approximately 45° and approximately 270°, and wherein for each bridge member, a sum of the arcuate extents of said bridge member and of a cut section adjacent to said bridge member in said end-to-end fashion is neither a whole number factor of 360° nor a multiple of 90°.

2. The component of claim 1, wherein said first transition region has a rigidity less than a rigidity of the relatively rigid region and greater than a rigidity of the relatively flexible region.

3. The component of claim 2, further comprising a second transition region between the first transition region and the relatively flexible region, wherein the second transition region has a rigidity less than the rigidity of the first transition region and greater than the rigidity of the relatively flexible region.

4. The component of claim 3, wherein the helically oriented pathway has a first pitch in the relatively rigid region, a second pitch in the relatively flexible region, and a third pitch in the first transition region, and a fourth pitch in the second transition region, and wherein the pitches are different from each other.

5. The component of claim 4, wherein the first pitch is greater than the third pitch, the third pitch is greater than the fourth pitch, and the fourth pitch is greater than the second pitch.

6. The component of claim 5, wherein said third pitch is between 75-90% of the first pitch, said fourth pitch is between 70-80% of the third pitch, and the second pitch is between 60-70% of the fourth pitch.

7. The component of claim 1, wherein the second pitch is between 20-75% of the first pitch.

8. The component of claim 1, wherein said first transition region comprises between two and four turns of the spiral ribbon.

9. The component of claim 1, wherein each of the relatively rigid region, the relatively flexible region, and the first transition region includes a plurality of bridge members.

10. The component of claim 1, wherein each bridge member is non-frangible during use within a body vascular system.

11. A neurovascular implant delivery system device movable through a microcatheter within a neurovascular vessel, comprising:

a generally hollow tubular portion including a spiral ribbon having adjacent turns, said ribbon being between a helically oriented pathway of a plurality of open sections alternating with a plurality of bridge members in end-to-end fashion along the helically oriented pathway, wherein each bridge member is out of axial alignment with each bridge member of the helically oriented pathway that is immediately adjacent thereto, wherein said spiral ribbon defines a relatively rigid region, a relatively flexible region, and a first transition region between the relatively rigid region and the relatively flexible region, and wherein each bridge member has an arcuate extent in a range of approximately 10° and approximately 65°, wherein each cut section has an arcuate extent in a range of approximately 45° and approximately 270°, and wherein for each bridge member, a sum of the arcuate extents of said bridge member and of a cut section adjacent to said bridge member in said end-to-end fashion is neither a whole number factor of 360° nor a multiple of 90°.

12. The neurovascular implant delivery system device of claim 11, wherein said spiral ribbon comprises a wound member and each bridge member comprises a weld between two adjacent turns of the spiral ribbon.

13. The neurovascular implant delivery system device of claim 11, wherein the bridge members define a substantially helical pattern different from the helically oriented pathway.

14. The neurovascular implant delivery system device of claim 11, wherein said helically oriented pathway is substantially defined by cut sections of an interrupted spiral cut, and wherein said bridge members comprise uncut sections of the interrupted spiral cut, said bridge members being non-frangible during use.

15. The neurovascular implant delivery system device of claim 11, wherein each bridge member has an arcuate extent of approximately 45°, and wherein each cut section has an arcuate extent of approximately 220°.

16. The neurovascular implant delivery system device of claim 11, wherein said spiral ribbon comprises a distal-most 15-30% of the neurovascular implant delivery system device.

17. The neurovascular implant delivery system device of claim 11, wherein the neurovascular implant delivery system device has an outer diameter no greater than 0.025 inch.

* * * * *